United States Patent [19]

Sharpe

[11] 4,228,688
[45] Oct. 21, 1980

[54] ACCURATE DISTANCE AMPLITUDE COMPENSATION

[75] Inventor: Donald E. Sharpe, Woodbury, Conn.

[73] Assignee: Automation Industries, Inc., Greenwich, Conn.

[21] Appl. No.: 15,112

[22] Filed: Feb. 26, 1979

[51] Int. Cl.³ ............................................. G01N 29/04
[52] U.S. Cl. ......................................... 73/631; 73/900
[58] Field of Search ........................ 73/1 R, 631, 900

[56] References Cited

U.S. PATENT DOCUMENTS

| | | | |
|---|---|---|---|
| 3,033,029 | 5/1962 | Weighart | 73/631 |
| 3,367,173 | 2/1968 | Uphoff | 73/631 |
| 3,690,153 | 9/1972 | Matay | 73/631 |
| 3,724,262 | 4/1973 | Niklas | 73/631 |
| 4,016,750 | 4/1977 | Green | 73/631 X |

*Primary Examiner*—Charles A. Ruehl
*Attorney, Agent, or Firm*—Francis N. Carten

[57] ABSTRACT

A function generator provides a voltage vs. time curve which is also applied to the oscilloscope and is adjusted by the operator to conform to the peak amplitudes of the displayed electrical pulses. During subsequent testing, this voltage function is applied to a control signal generator which, in accordance with a predetermined relationship, modifies the voltage function into a control signal which is applied to the receiver. The control signal varies the receiver gain with time to attenuate and equalize the displayed pulses to a preselected amplitude.

The equalized pulses corresponding to the equal sized reflectors are dependent upon only the size of the reflector and are independent of the depth of the discontinuities within the test blocks. As a result of the adjustment to the receiver gain by the control signal, the magnitudes of all displayed echo pulses from workpieces subsequently tested by the system will be dependent only upon the sizes of the corresponding discontinuities in the workpieces.

31 Claims, 3 Drawing Figures

ACCURATE DISTANCE AMPLITUDE COMPENSATION

BACKGROUND OF THE INVENTION

The present invention relates to distance amplitude compensation techniques used in connection with ultrasonic pulse echo testing for flaws and discontinuities in a workpiece.

The use of ultrasonic pulse echo techniques to test workpieces is well known. High frequency electrical pulses are applied to a transducer which converts them into ultrasonic pulses which are applied to an entering surface of a workpiece to be tested. The ultrasonic pulses are reflected back towards the entering surface of the workpiece by discontinuities such as defects within the workpiece. The same, or a different, transducer receives the reflected pulses and reconverts them into electrical pulses. The electrical pulses may be displayed on a cathode ray tube. The above-described testing procedure is further explained in U.S. Pat. No. 2,280,226 issued to F. A. Firestone on Apr. 21, 1942.

If one or more test blocks are provided with identically sized reflectors spaced apart and at varying depths therein, the amplitudes of the displayed electrical pulses are initially relatively small, increase in magnitude to a maximum value as the depth of the reflectors within the workpiece increases, and then decrease in amplitude as the depth of the reflectors within the workpiece is still further increased. Thus, the magnitudes of the reflected pulses are dependent upon both the sizes of the corresponding reflectors and the depths of the reflectors within the workpiece. (The term "depth," as used above, is intended to mean the distance between the entrance surface and the reflector within the workpiece).

The reason for the above described phenomenon in which the magnitude of a reflected pulse is dependent upon both the size of the reflector and its depth within the workpiece is due to the "near field" and "far field" effects as well as attenuation in the material. The "near field zone" is the portion of the workpiece closest to the entrance surface in which the reflected pulses increase in size. The maximum amplitude of the reflected pulse is realized at a depth referred to as the "near field limit". As the depth of the reflector is further increased beyond the near field limit and into the "far field", the magnitudes of the reflected pulses progressively decrease due to the diverging beam and to attenuation by the test material. The near field and far field effects of a testpiece are discussed in U.S. Pat. Nos. 3,033,029 and 4,056,971.

In practice, only the pulse echo from a single reflector (or test hole) can be displayed at any one location of the transducer. Thus, only one point on the composite curve representing the echo signals can be displayed on the cathode ray tube at any given instant of time. The pulse echo displayed on the cathode ray tube at any given instant corresponds to the single test hole which is reflecting the applied ultrasonic energy at that instant.

One form of a distance amplitude compensation system varies the gain of the receiver (which receives the reflected pulse echoes from a testpiece) to compensate for the above-described near field and far field effects. The objective of a distance amplitude compensation system is to assure that all pulse echoes from identically sized defects are displayed as equal magnitudes, irrespective of the depth of the defects within the workpiece. The amplitudes of all displayed echoes are then functions of only the size of their corresponding defects.

A known disadvantage of conventional distance amplitude compensation systems is that complicated trial and error techniques are required to adjust the gain of the receiver to eliminate the near field and far field effect factors from the reflected pulse echoes. Since only one pulse echo from the test holes of a test block can be displayed on a cathode ray tube at any instant of time, many passes or scans of the transducer over each test hole are required to make an optimum adjustment of the magnitude of the echo. In practice, it has also been found that adjustment of one pulse echo affects the magnitudes of adjacent echoes, thereby requiring many additional scans and adjustments to provide optimum compensation for all pulse echoes. Equalization of the pulse echoes by varying the receiver gain with time using such trial and error techniques is time consuming, laborious and subject to errors.

An example of a conventional distance amplitude compensation system is disclosed in U.S. Pat. No. 3,033,029 (Weighart). Other conventional systems are known to those skilled in the art.

U.S. Pat. No. 4,056,971 describes a system which does not involve varying the receiver gain with time and thus avoids this aspect of the set-up problem for the curveshape generator. It does not compensate for the near field and far field effect of the workpiece by equalizing the displayed signals reflected from a given sized defect irrespective of the depth of the defect. Instead, this patent discloses a system which compares a reference distance amplitude response curve (of uncompensated reflected pulse signals from a given size defect at various depths within a test piece) with the uncompensated reflected signals of the workpiece being tested. If the signals from the workpiece under test exceed the reference signal, an alarm is actuated.

It is the main object of the present invention to provide a distance amplitude compensation system which enables an operator of the system to readily equalize the magnitudes of reflected pulse signals corresponding to given size defects at predetermined levels by varying the gain of the receiver of the system in accordance with a predetermined relationship, thereby eliminating the trial and error techniques of conventional systems.

SUMMARY OF THE INVENTION

The preferred embodiment of the invention provides a distance amplitude compensation system for use in correcting the output from an ultrasonic pulse echo circuit used for testing materials for discontinuities. (As used herein, the term "discontinuity" is intended to mean flaws, defects or other structural irregularities within a material which will reflect ultrasonic pulses.) The distance amplitude compensation system includes means for automatically adjusting the gain-time function of a receiver so that the amplitudes of reflected pulse echos from workpieces being tested are a function only of the size of discontinuities within the workpiece, and are independent of the positions of the discontinuities.

Ultrasonic pulses are applied to one or more test blocks having equal sized discontinuities (or reflectors) at varying distances from the entering surface of the test blocks. Reflected ultrasonic pulse echoes returned from the discontinuities are received by a transducer, converted into electrical pulses, and applied to a first input of a receiver.

A function generator provides a time varying voltage function which is adjusted to conform to the differing amplitudes of the reflected electrical pulses, which are dependent upon the depth of the corresponding discontinuities within the test blocks. The differing amplitudes of the reflected pulses, which are separately displayed on the cathode ray tube at different instants of time, are marked on the screen of the cathode ray tube with, for example, a grease pencil, during a single scan of the test holes by the transducer. The function generator is then adjusted to provide a time varying voltage function matching the markings on the screen, thereby providing a continuous time varying voltage function simulating the reflected pulse echoes.

This time varying voltage function is applied to the input of a control signal generator which, in accordance with a predetermined relationship, modifies the voltage function into a control signal. The control signal is applied to a second input of the receiver to automatically vary the gain of the receiver to attenuate and equalize the amplitudes of the electrical pulses applied thereto. Means are provided to adjust the control signal and thereby select the level at which the reflected electrical pulses are equalized. Once the time varying voltage function simulating the pulse echoes is determined from a single scan of the test blocks, the control signal required to adjust the gain of the receiver is calculated in accordance with a predetermined relationship. The pulse echoes are automatically equalized without resort to the complicated trial and error techniques of the known systems.

Because of the gain adjustment to the receiver by the control signal, the amplitudes of electrical pulses corresponding to echoes returned from discontinuities in any test pieces subsequently tested will be a function of only the size of the discontinuities, and will be independent of the depth of the discontinuities within the workpieces.

A cathode ray tube (CRT) may be provided to selectively display the voltage function from the function generator and the electrical pulses corresponding to returned pulse echoes. The horizontal axis of the CRT is in units of time and corresponds to the depth of discontinuities within a workpiece being tested, while the vertical axis of the CRT is in units of voltage and corresponds to the sizes of discontinuities detected.

DESCRIPTION OF THE PREFERRED EMBODIMENT OF THE INVENTION

Figure 1:
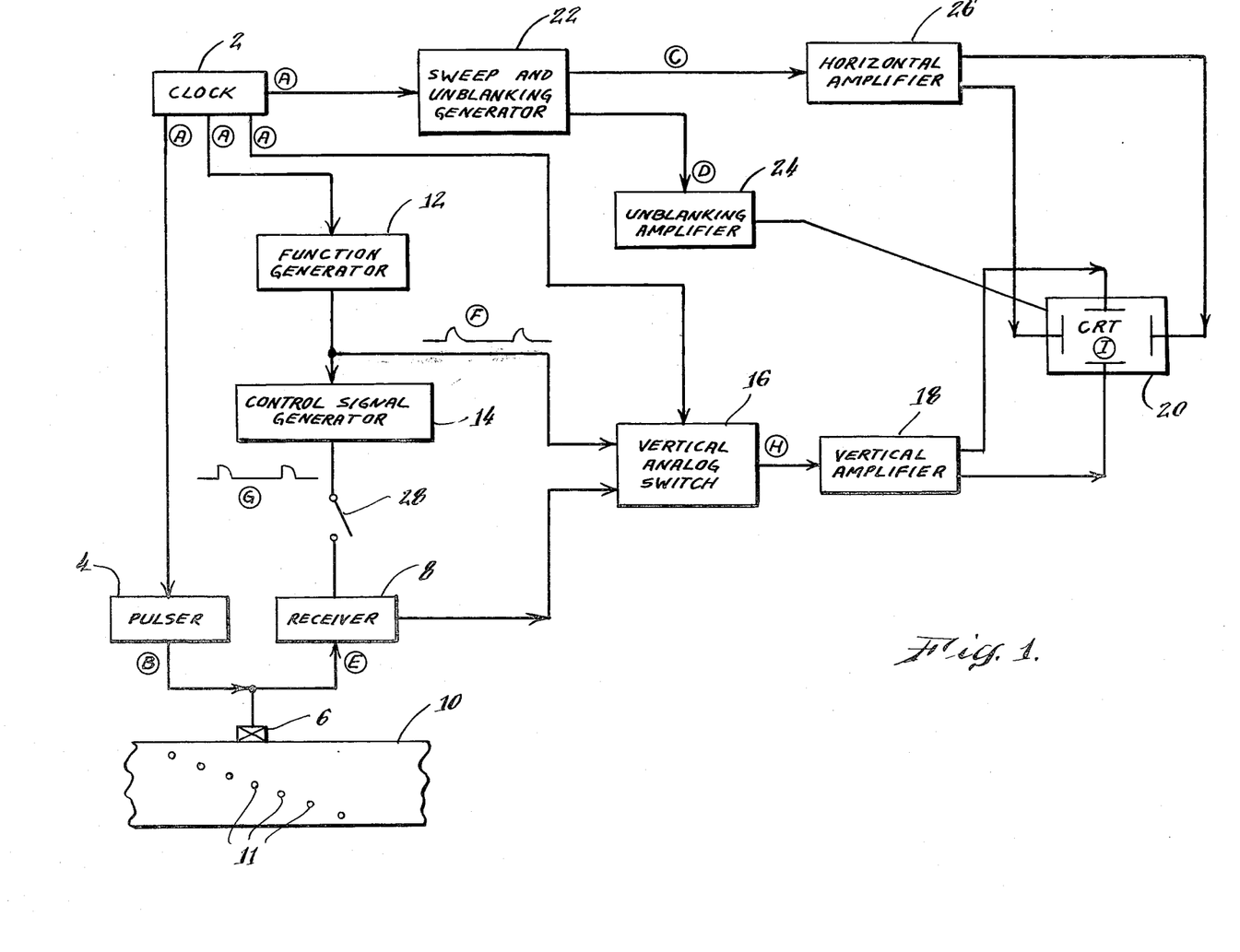
FIG. 1 is a block diagram of an ultrasonic testing system incorporating distance amplitude compensation in accordance with the present invention.

One embodiment of an ultrasonic pulse echo testing circuit including a distance amplitude compensation system in accordance with the present invention will be described with reference to the drawings. A clock 2 is coupled to a pulser 4 and periodically provides a clock pulse (as shown by FIG. 2A) to a pulser 4. An ultrasonic transducer 6 is electrically coupled to the output of the pulser 4 and to the input of a receiver 8. It is ultrasonically coupled to the surface of a test block 10 having equally sized discontinuities which may be, for example, drilled holes 11 spaced apart from each other in the test block at varying distances away from the entering surface.

The distance amplitude compensation system includes a function generator 12 and a control signal generator 14. The input of the function generator 12 is connected to one output of the clock 2. The output of the function generator is coupled to the control signal generator 14, and is also coupled to a standard cathode ray tube (CRT) 20 through a vertical analog switch 16 and a vertical amplifier 18. The vertical amplifier 18 is connected to the vertical plates of the cathode ray tube.

The control signal generator 14 is selectively coupled to the receiver 8 by switch 28. When the switch 28 is in its "ON" position, the control signal generator applies a control signal to the input of the receiver 8. When the switch is in its "OFF" position, the control signal generator is disconnected from the receiver.

The ultrasonic pulse echo circuit also includes a sweep and unblanking generator 22, which is connected to an output of the clock 2. The output of the generator 22 is applied to both an unblanking amplifier 24 and a horizontal amplifier 26. The unblanking amplifier 24 is coupled to the CRT 20 and controls the intensity modulation thereof, and the horizontal amplifier is coupled to the horizontal plates of the CRT 20.

The output of the receiver 8 is coupled to the vertical plates of the cathode ray tube 20 through the vertical analog switch 16 and the vertical amplifier 18. The vertical analog switch is also coupled to the clock 2.

The clock pulses are shown in FIG. 2A as rectangular waves and their frequency can vary within the range of 100 hertz to 10 kilohertz. For most applications, the clock will be set to generate the rectangular pulses at about 1 kilohertz. They are applied to the input of the pulser 4 which, in response thereto, generates electrical pulses corresponding to those shown in FIG. 2B. These electrical pulses are applied to the transducer 6, which converts them into ultrasonic pulses which are then applied to the test block 10.

The test block 10, which has a plurality of equal sized reflectors 11 defined at various depths therein and spaced apart from each other, receives ultrasonic pulses from the transducer 6. Although the drawing illustrates a single test block having many reflectors, in practice several test blocks each having fewer reflectors can also be used. Because of near field and far field effects and attenuation of the test block 10, the reflected ultrasonic pulse echoes from the test block are of unequal amplitudes. These echoes are reflected back towards the transducer 6, where they are reconverted into electrical pulses and applied to the receiver 8. FIGS. "2E" and "$2I_1$" illustrate the varying amplitudes of these electrical pulses. In practice, the transducer is moved relative to the entering surface of the test block and only a single echo corresponding to the reflector which is reflecting the applied ultrasonic energy is sensed at any instant. The solid line pulse shown within the envelope of FIG. $2I_1$ represents a single echo displayed on the screen of a cathode ray tube at an arbitrary time during the scan of the test block, while the pulses shown in broken lines correspond to other reflectors in the test block which have been or will be displayed at other times. Although the same transducer 6 of the present embodiment converts electrical pulses into ultrasonic pulses and reconverts ultrasonic pulse echoes into electrical pulses, two separate transducers can also be employed to perform these functions.

The function generator 12, which is coupled to the clock 2, provides a voltage function (as shown by FIG. 2F) which is adjusted by the operator to conform to the peak amplitudes of the reflected electrical pulse echoes from the test block 10. Function generators of this type are known to those skilled in the art and one type of such generator is described in U.S. Pat. No. 3,033,029.

Figure 2:
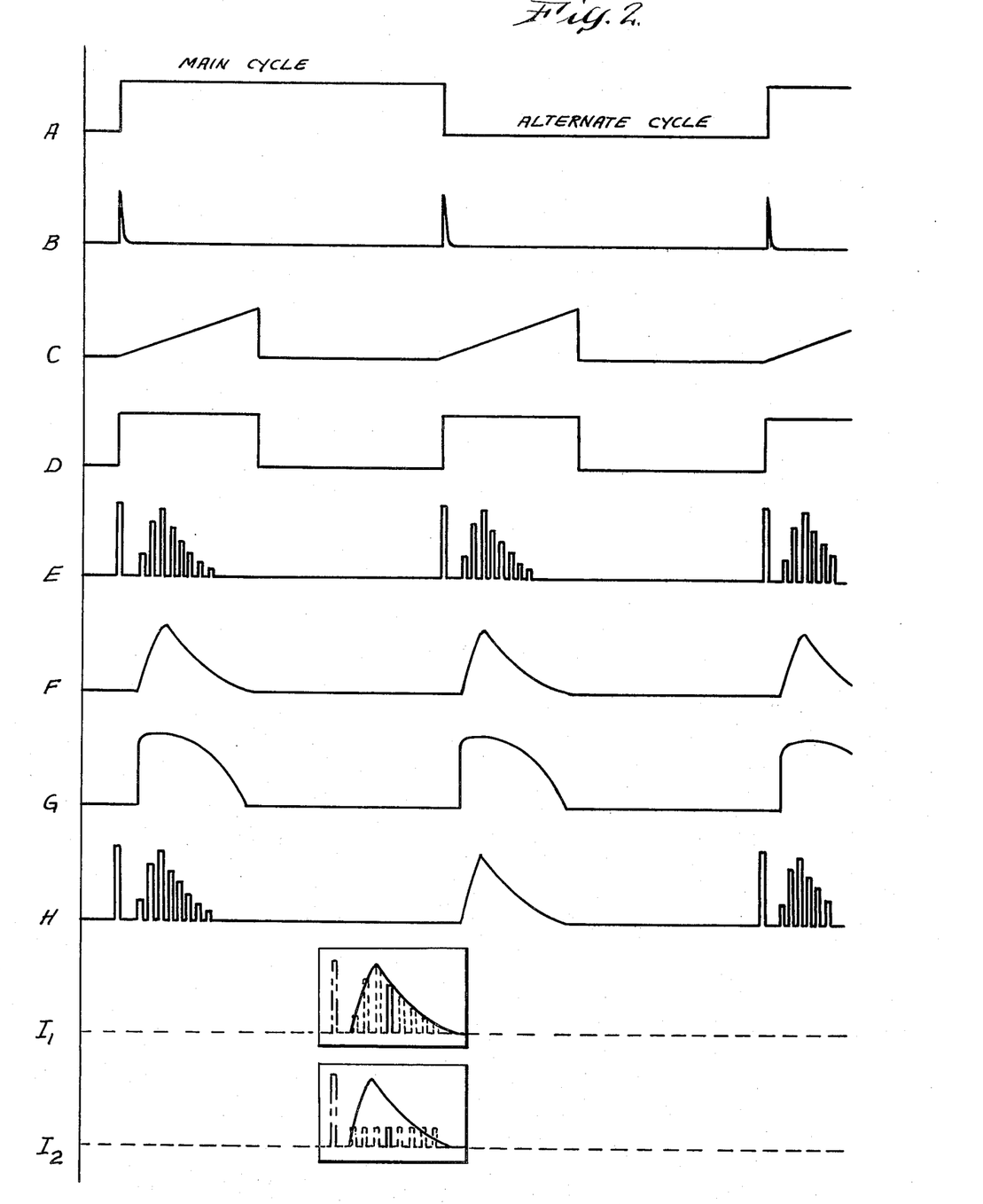
FIGS. 2A through 2I are timing diagrams illustrating the operation of the present invention.

With reference to FIGS. 1 and 2, the adjustment of the voltage function of the function generator is performed as follows. The switch 28, which is disposed between the control signal generator 14 and the receiver 8, is moved into its open position. Electrical pulses from the transducer 6, corresponding to each of the ultrasonic pulse echoes returned from the reflectors within the test block 10, are applied to the vertical plates of the cathode ray tube through the vertical amplifier 18 at different instants of time during the scan of the test block. The peaks of the different pulse echoes are then marked on the screen of the cathode ray tube (as for example, by a grease pencil). FIG. 2E illustrates the display of the pulse echoes on the screen (For convenience, all echoes have been shown at once). After the scan of the test block is completed and the peaks of all pulse echoes have been marked on the screen, the function generator is adjusted to provide a time varying continuous voltage function matching the peaks of the pulse echoes marked on the screen. FIG. 2F illustrates the adjusted time varying voltage function of the function generator, and FIG. $2I_1$ shows that this voltage function matches the peaks of the pulse echoes.

The voltage function 2F of the function generator 12 is also applied to the control signal generator 14. The control signal generator modifies the voltage function applied thereto into a control signal (as shown by FIG. 2G) in accordance with a predetermined relationship. The control signal 2G is selectively coupled to the receiver 8 by the switch 28.

The control signal 2G is a time varying voltage function which, when applied to receiver 8 simultaneously with each of the reflected electrical pulse echoes from the test block, varies the gain of the receiver to attenuate and equalize the amplitudes of all the reflected pulses at a predetermined amplitude, as shown by FIG. $2I_2$.

It is important to note that in typical gain control circuitry, the voltage function 2F which simulates the distance-amplitude curve, and the control signal voltage function 2G required by the receiver gain control input for optimum compensation, are not the same. Accordingly, voltage function 2F cannot be fed directly into the receiver gain control input. These two functions are, however, mathematically related, and as noted above, the control signal voltage is derived by modifying the voltage function 2F in accordance with a predetermined relationship.

This distinction is important because, in the past, attempts were made to vary the receiver gain by applying the voltage function 2F directly to the receiver. Such attempts were unsuccessful in equalizing the pulse echoes, and variations of the applied voltage function by trial and error techniques was still necessary to achieve optimum adjustment of the receiver gain to equalize the pulse echoes. In contrast, the control signal generator disclosed herein modifies the voltage function 2F to provide a separate and distinct control signal 2G which is applied to the receiver. The control signal is calculated from a predetermined relationship (to be discussed below) to provide optimum adjustment to the gain of the receiver for equalizing the pulse echoes from the test blocks without resort to any trial and error techniques.

When switch 28 is in its OFF position, no control signal is applied to the receiver 8, and the output at the receiver 8 represents the reflected pulse echoes from the test block 10. However, when the switch 28 is ON and the transducer is brought over each test hole 11, the output of the receiver 8 is a pulse of amplitude equal to those of the other test holes. Each of these equal amplitude pulses corresponds to the equal sized reflectors within the test block. By equalizing the amplitudes of the pulse echoes, the control signal has adjusted the gain of the receiver to compensate for the near field and far field effects of the test block. That is, equal size electrical pulse echoes correspond to equal size reflectors, irrespective of the positions of the reflectors within the test block 10. Similarly, the amplitude of each reflected pulse echo from a discontinuity in a subsequently tested workpiece will also be a function of only the size of the discontinuity.

The sweep and unblanking generator 22, the unblanking amplifier 24, the horizontal amplifier 26, the vertical analog switch 16 and the vertical amplifier 18 are conventional elements and will be briefly discussed as follows.

The clock 2, in addition to applying a pulse to the pulser 4, applies a pulse to the sweep and unblanking generator 22, which generates a saw-tooth wave as shown in FIG. 2C. This saw-tooth wave is coupled to the horizontal amplifier 26, which is coupled to the horizontal control plates of the standard CRT 20. A second output of the sweep and unblanking generator 22 provides a rectangular pulse (as shown in FIG. 2D) to the unblanking amplifier 24. The unblanking amplifier, which is coupled to the CRT 20, controls the intensity modulation of the CRT to enable it when the unblanking amplifier is actuated by the rectangular pulse applied thereto.

Thus, the sweep and unblanking generator 22 is operative to generate a saw-tooth sweep signal to control the horizontal trace of the CRT for the time duration of the sweep signal shown by FIG. 2C. The rectangular pulse output of the sweep and unblanking generator actuates the CRT to enable the horizontal trace to appear for the duration of the unblanking pulse shown by FIG. 2D.

Referring to FIG. 2, it is seen that the clock pulse 2A includes a main pulse cycle and an alternate pulse cycle. During the main pulse cycle, the output from the receiver 8 is displayed on the CRT 20. During the alternate pulse cycle, the output from the function generator is displayed on the CRT screen. The alternate display of these two functions is controlled by the vertical analog switch 16, which is directly coupled to the clock 2 to receive the main and alternate clock pulses. FIG. 2H illustrates the time varying alternate displays of the output of the receiver 8 and the output of the function generator 12 on the CRT screen when the switch 28 is opened.

ADJUSTMENT OF RECEIVER GAIN

As noted before, the control signal generator 14 receives a voltage function from the function generator 12 and generates a control signal in response thereto. This control signal is applied to one input of the receiver 8, and varies the gain of the receiver with time to attenuate the amplitudes of the reflected electrical pulse echoes provided thereto.

In order to assure that the control signal will equalize the reflected electrical pulse echoes at the receiver, an equation was empirically derived to establish the control signal amplitude required to attenuate each echo peak to a common level. This equation was derived by plotting a series of linearly decaying echo peaks varying in magnitude from ten vertical CRT divisions to one vertical CRT division. The voltage required to attenuate each of these peaks to a magnitude of one CRT division was experimentally determined, and the following Equation 1 was derived from this experimentation.

$$V_C = F_S - \left[ \frac{R}{I} (F_S - I) \right] \quad \text{Equation 1}$$

Where:
$V_C$ = the voltage applied from the control signal generator to the receiver 8,
$F_S$ = full scale in CRT divisions (10 divisions),
$R$ = amplitude of smallest reflected pulse in CRT divisions (1 division) and the value at which all pulses are to be attenuated,
$I$ = initial (unattenuated) pulse echo amplitudes in CRT divisions Since any value of R greater than one division can be reduced to one division by multiplying it by 1/R, and since any value of I greater than R can be proportionally reduced by multiplying it by 1/R, Equation 1 can be expressed as follows:

$$V_C = F_S - \frac{\frac{1}{R}(R)}{\frac{1}{R}(I)} \left( F_S - \frac{1}{R}(I) \right),$$

which reduces to $$V_C = F_S - \frac{F_S - \frac{I}{R}}{\frac{I}{R}} \quad \text{Equation 2}$$

In a practical circuit, 10 CRT divisions is equal to 5 volts, each division corresponding to 0.5 volts. To proportionally reduce the values of R and I in Equation 1, each of these values is multiplied by 0.5/R, resulting in $$V_C = F_S - \left[ \frac{\frac{0.5}{R} R}{\frac{0.5}{R} I} F_S - \frac{0.5}{R} I \right] \quad \text{Equation 3}$$

in which $V_C$ is the voltage required to vary the receiver to reduce a pulse echo I to the level R.

Substituting $F_S$ (full scale) = 5 volts. Equation 3 is expressed as follows:

$$V_C = 5.5 - (5R/I) \quad \text{Equation 4}$$

where R and I are in volts.

Equations 1-4 define a relationship in which a voltage $V_C$ applied to the receiver 8 will vary the gain of the receiver to attenuate a pulse echo of magnitude I to a magnitude of R. The control signal generator 14, which generates the $V_C$ voltage, is provided with the value I from the function generator 12. As previously discussed, the peaks of the time varying voltage function correspond to the peaks of the pulse echoes, which in turn, correspond to the values of I of Equations 1-4.

Thus, Equations 1-4 define the relationship between the magnitudes of the pulse echoes and the required time varying control signal needed to attenuate the magnitudes of each of the pulse echoes to a predetermined level.

Figure 3:
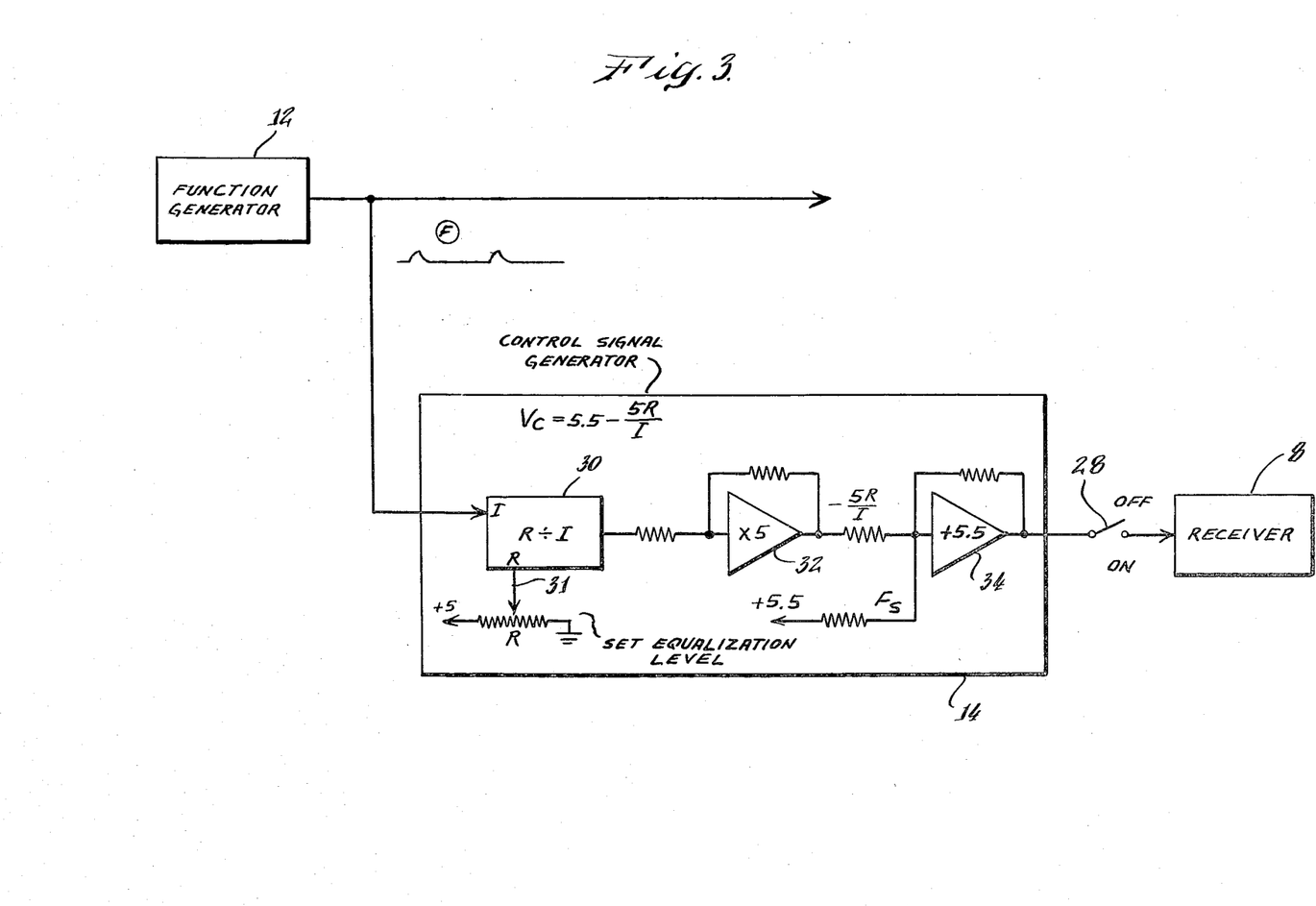
FIG. 3 is a circuit diagram of an embodiment of the control signal generator shown in FIG. 1.

FIG. 3 illustrates a block diagram of a control signal generator 14 constructed to generate the voltage function $V_C$ (the control signal which varies the receiver gain) defined by Equation 4. Such a control signal generator can include an analog computer.

Specifically referring to FIG. 3, a divider 30 is connected to the output of the function generator 12 which provides the divider with the "I" function—the "envelope" of observed pulse heights from the sample material. The voltage divider also includes means 31 for setting the "R" value (the value in volts at which the amplitudes of the pulse echoes will be equalized) of Equation 4.

The divider 30 computes the value of R/I and applies the result to a multiplier 32. The multiplier generates −(5R/I) and applies this value to the input of an adder 34, which generates an output voltage proportional to 5.5−(5R/I), the value of $V_C$ in accordance with Equation 4. This voltage is applied to one input of the receiver 8. As indicated above, the "R" value (at which the reflected pulse echoes will be equalized) will usually be set on the divider 30 at the amplitude of the smallest reflected pulse echo.

The control signal generator 14 provides the control signal ($V_C$) to one input of the receiver 8. A second input to the receiver 8 from the transducer 6 represents, in voltage, the values of the amplitudes of the reflected pulse echoes from the test block 10. The control signal varies the gain of the receiver to attenuate and equalize the amplitudes of the reflected pulse echoes at a preselected value, and the equalized pulses are displayed on the screen of the CRT 20.

The displayed equalized pulse echoes are a function of only the magnitude of the equal sized discontinuities in the test block and are independent of the depth of the discontinuities therein. As a result of the adjustment of the receiver gain by the control signal applied thereto, the amplitudes of pulse echoes of any workpieces subsequently tested for discontinuities will also be a function of only the size of any discontinuities within the workpiece. The difference in size of the various discontinuities within a workpiece being tested can be readily compared by observing their relative amplitudes on the CRT screen.

As shown in FIGS. $2I_1$ and $2I_2$, the reflected pulse echoes are separated from each other by a certain distance on the horizontal axis of the CRT. The position of the larger first pulse, which represents the pulse from pulser 4, corresponds to the entrance surface of the work block 10. The position of the subsequent pulses are proportional to the time necessary for the ultrasonic pulses entering the workpiece and propagating therethrough to reach the position of a given discontinuity and be reflected back to the entering surface of the workpiece. Because the first pulse displayed in FIGS. $2I_1$ and $2I_2$ represents the entering surface of the workpiece, the distance between the first pulse and each of the subsequent pulses represents the relative depth of the respective discontinuities within the workpiece.

Thus, the presently described embodiment of the invention provides both a visual indication of the magnitudes of discontinuities and the depth of the respective discontinuities within the workpiece being tested.

Furthermore, the disclosed system can be quickly and easily put into operation. Once the characteristic time varying function simulating the pulse echoes is determined from the test blocks, the operator of the system is only required to set the level to which the magnitudes of all pulse echoes will be attenuated. The operator is not required to perform any trial and error adjustments to equalize the pulse echoes.

It is believed that modifications and variations of the above-described embodiment of the present invention will be apparent to those skilled in the art. Accordingly, the disclosed embodiment is intended to be illustrative only, and not restrictive of the scope of the invention, that scope being defined by the following claims and all equivalents thereto.

What is claimed is:

1. A system for ultrasonic pulse echo testing including a compensation system for equalizing the amplitudes of ultrasonic pulse echoes reflected from a workpiece by equal sized discontinuities therein irrespective of the depths of said discontinuities within said workpiece, said system for ultrasonic pulse echo testing comprising:

means for applying ultrasonic pulses to said workpiece to be tested;

a transducer operatively associated with said workpiece for receiving ultrasonic pulse echoes reflected from discontinuities within said workpiece and for converting said reflected ultrasonic pulse echoes into reflected electrical pulses;

a receiver having a first input operatively associated with said transducer for receiving said reflected electrical pulses from said transducer;

a function generator for generating a voltage function having a characteristic curve which is adjusted to conform to the amplitudes of reflected electrical pulses from a testpiece having a plurality of equally sized discontinuities defined at different depths within said testpiece;

control signal generator means operatively associated with said function generator for receiving said voltage function from said function generator and for modifying said voltage function, in accordance with a predetermined relationship, into a control signal having a value which, when applied to said receiver will vary the gain of said receiver to attenuate and substantially equalize reflected electrical pulses representative of pulse echoes reflected from substantially equal sized discontinuities within said test piece; and means for selectively applying said control signal from said control signal generator means to a second input of said receiver to vary the gain of said receiver, whereby the attenuated amplitudes of reflected electrical pulses representative of pulses echoes from workpieces subsequently tested are proportional to the size of corresponding reflecting discontinuities within said workpieces and are substantially independent of the depth of said discontinuities within said workpieces.

2. A system as claimed in claim 1 wherein said means for applying said control signal is a switch, said control signal being applied to said receiver only when said switch is in an operative position.

3. A system as claimed in claim 2 wherein said means for applying ultrasonic pulses to said workpiece includes means for supplying electrical pulses to said transducer, whereby said electrical pulses are converted into ultrasonic pulses by said transducer.

4. A system as claimed in claim 1 further including a cathode ray tube coupled to the output of said receiver for displaying said reflected electrical pulses.

5. A system as claimed in claim 4 further including means for connecting said cathode ray tube to said function generator for displaying said voltage function on said cathode ray tube.

6. A system as claimed in claim 5 further including means for synchronizing said means for applying said ultrasonic pulses, said cathode ray tube and said function generator such that they are all actuated simultaneously.

7. A system as claimed in claim 4 including means for synchronizing said means for applying said ultrasonic pulses and said cathode ray tube.

8. A system as claimed in claim 7 wherein said means for synchronizing includes a clock for providing actuating clock pulses to said means for applying ultrasonic pulses, and means for simultaneously applying said actuating clock pulse to the vertical and horizontal plates of said cathode ray tube.

9. In a system for ultrasonic pulse echo testing having means for applying ultrasonic pulses to a workpiece, transducer means for converting ultrasonic pulse echoes reflected from said workpiece into reflected electrical pulses, a receiver for receiving said reflected electrical pulses, and means for displaying electrical signals, the improvement comprising:

means for generating a voltage function having a characteristic curve which is adjusted to conform to the amplitudes of electrical pulses corresponding to ultrasonic pulse echoes reflected from equal sized discontinuities at varying depths within a testpiece;

control signal generator means for receiving and modifying said voltage function, in accordance with a predetermined relationship, into a control signal having a value which, when applied to said receiver, will vary the gain of said receiver to attenuate and substantially equalize reflected electrical pulses representative of pulse echoes returned from equal sized discontinuities in said testpiece; and means for selectively applying said control signal to said receiver for varying the gain of said receiver, whereby the attenuated amplitudes of reflected electrical pulses representative of pulse echoes from workpiece subsequently tested are proportional to the size of corresponding reflecting discontinuities within said workpieces, and are substantially independent of the depth of said discontinuities within said workpieces.

10. A system as claimed in claim 9 wherein said means for applying said control signal is a switch interposed between said control signal generator means and said receiver, said control signal being applied to said receiver only when said switch is in an operative position.

11. A system as claimed in claim 10 wherein said means for displaying electrical signals includes means operatively associated with said receiver for visually displaying said reflected electrical pulses from a workpiece being tested when said switch means is in said operative position.

12. A system as claimed in claim 11 wherein said means for displaying electrical signals further includes means operatively associated with said function generator for visually displaying said voltage function.

13. A system as claimed in claim 12 wherein said means for visually displaying includes a cathode ray tube.

14. A system as claimed in claim 11 wherein said means for visually displaying includes a cathode ray tube.

15. A system as claimed in claim 14 wherein the screen of said cathode ray tube is divided into a plurality of equal vertical divisions and each of said displayed reflected electrical pulses is of an amplitude which corresponds to one of said vertical divisions, wherein said control signal is determined by the following relationship:

$$V_C = F_S - \frac{R}{I}(F_S - I)$$

where
$V_C$ = the control signal voltage,
R = the level in vertical divisions to which the amplitudes of the reflected electrical pulses are to be reduced,
I = the level in vertical divisions of the reflected electrical pulse to be reduced, and
$F_S$ = the number of divisions on the full vertical scale of the cathode ray tube.

16. A system as claimed in claim 14 wherein the screen of said cathode ray tube is divided into a plurality of equal vertical divisions and each of said displayed reflected electrical pulses is of an amplitude which corresponds to one of said vertical divisions, wherein said control signal produced by said control signal generator means to vary the gain of said receiver for equalizing the amplitudes of said reflected electrical pulses associated with said testpiece having equal sized discontinuities to the level of any of said vertical divisions is determined by the following relationship:

$$V_C = F_S - \frac{F_S - \frac{1}{R_v}(I)}{\frac{1}{R_v}I}$$

where
$V_C$ = the control signal voltage,
$R_v$ = the amplitude to which all reflected pulses are to be reduced ($R_v$ must be equal to or less than the amplitude of the smallest reflected electrical pulse, and must be greater than or equal to one vertical CRT division),
I = the level in vertical divisions of the reflected electrical pulse to be reduced, and
$F_S$ = the number of divisions on the full vertical scale of the cathode ray tube.

17. A system as claimed in claim 14 wherein the screen of said cathode ray tube is divided into 10 vertical divisions and each of said divisions represents a voltage of 0.5 volts, wherein said control signal produced by said control signal generator means to vary the gain of said receiver for equalizing the amplitudes of said reflected electrical pulses associated with said testpiece having equal sized discontinuities is determined by the following relationship:

$$V_C = 5.5 - (5R/I),$$

where
$V_C$ = the control signal voltage,
R = the level in volts to which the amplitudes of the reflected electrical pulses are equalized, and
I = the initial amplitude in volts of the reflected electrical pulse to be equalized.

18. A system as claimed in claim 17 wherein said "I" value is provided to said control signal generator means from said function generator.

19. A system as claimed in claim 17 wherein said control signal generator means includes means for adjusting said "R" value,
whereby said level at which said reflected electrical pulses associated with said testpiece are to be equalized is adjustable.

20. A system as claimed in claim 17 wherein said control signal generator means includes means for receiving said "I" value from said function generator, means for dividing said "R" value by said "I" value to produce a first quotient, means for multiplying said first quotient by 5 to produce a first product, and means for subtracting said first product from the value 5.5 to produce said value of "$V_C$" required to reduce the amplitude of "I" of said reflected electrical pulses to said value of "R".

21. A system as claimed in claim 20 wherein said value of "R" is equal to 0.5 volts.

22. A system as claimed in claim 9 further including means for synchronizing the actuation of said means for applying said ultrasonic pulses with the actuation of said means for displaying electrical signals,
whereby said means for displaying electrical signals is actuated simultaneously with the application of said ultrasonic pulses to said workpiece.

23. A system as claimed in claim 22 wherein said means for synchronizing includes a clock coupled to both said means for applying said ultrasonic pulses and said means for displaying electrical signals,
said clock emitting an actuating clock pulse simultaneously to both said means for applying ultrasonic pulses and said means for displaying electrical signals for simultaneous actuation thereof.

24. A system as claimed in claim 23 further including second means for synchronizing the actuation of said function generator with actuation of said means for displaying electrical signals and said means for applying ultrasonic pulses.

25. A system as claimed in claim 24 wherein said second means for synchronizing includes means for coupling said clock to said function generator,
wherein said actuating pulse of said clock actuates said voltage generator simultaneously with said actuation of said means for applying ultrasonic pulses and said actuation of said means for displaying electrical signals.

26. A method of ultrasonic pulse echo testing of workpieces for discontinuities using a system including means for applying ultrasonic pulses to said workpieces, means for transducing pulse echoes reflected from said discontinuities into electrical pulses, and a receiver for receiving said electrical pulses, the steps of said method comprising:

applying ultrasonic pulses to a testpiece having a plurality of equal sized discontinuities defined at various depths therein;

generating a voltage function which is adjusted to conform to the amplitudes of electrical pulses corresponding to ultrasonic pulse echoes from said equal sized discontinuities within said testpiece;

modifying said voltage function, in accordance with a predetermined relationship, into a control signal of a value which, when applied to said receiver, will vary the gain of said receiver to attenuate and equalize said electrical pulses at a predetermined value; and applying said control signal to said receiver to vary the gain of said receiver, whereby the amplitudes of electrical pulses corresponding to discontinuities within workpieces being tested are a function of the size of said discontinuities, and are substantially independent of the depth of said discontinuities within said workpieces.

27. A method as claimed in claim 26 further including the step of visually displaying said electrical pulses.

28. A method as claimed in claim 27 wherein a cathode ray tube is provided for visually displaying said electrical pulses.

29. A method as claimed in claim 28 wherein the screen of said cathode ray tube is divided into a plurality of equal vertical divisions and said predetermined relationship for generating said control signal is:

$$V_C = F_S - \frac{R}{I}(F_S - I)$$

where $V_C$ = the control signal voltage, $R$ = the level in vertical divisions to which the amplitudes of the reflected electrical pulses are to be reduced, $I$ = the level in vertical divisions of the reflected electrical pulse to be reduced, and $F_S$ = the number of divisions on the full vertical scale of the cathode ray tube.

30. A method as claimed in claim 28 wherein the screen of said cathode ray tube is divided into a plurality of equal vertical divisions and the predetermined relationship for generating said control signal is:

$$V_C = F_S - \frac{F_S - \frac{1}{R_v}I}{\frac{1}{R_v}I}$$

where $V_C$ = the control signal voltage, $R_v$ = the amplitude to which all reflected pulses are to be reduced ($R_v$ must be equal to or less than the amplitude of the smallest reflected electrical pulse, and must be greater than or equal to one vertical CRT division), $I$ = the level in vertical divisions of the reflected electrical pulse to be reduced, and $F_S$ = the number of divisions on the full vertical scale of the cathode ray tube.

31. A method as claimed in claim 28 wherein the screen of said cathode ray tube is divided into ten equal vertical divisions and each of said vertical divisions represents a voltage of 0.5 volts, wherein said predetermined relationship for generating said control signal is:

$$V_C = 5.5 - (5R/I),$$

where $V_C$ = the control signal voltage, $R$ = level in volts to which the amplitudes of the reflected electrical pulses are equalized, and $I$ = the initial amplitude in volts of the reflected electrical pulse to be equalized.

* * * * *